United States Patent
Tsang et al.

(10) Patent No.: US 7,410,771 B2
(45) Date of Patent: Aug. 12, 2008

(54) **REAGENT AND METHOD FOR DETECTING A *CRYPTOSPORIDIUM PARVUM* SPOROZOITE ANTIGEN**

(75) Inventors: Victor C. W. Tsang, Decatur, GA (US); Jeffrey L. Call, Logan, UT (US); Yeuk-mui Lee, Lilburn, GA (US); Kathy Hancock, Atlanta, GA (US)

(73) Assignee: The United States of America as represented by the Department of Health and Human Services, Center for Disease Control and Prevention, Washington, DC (US)

( * ) Notice: Subject to any disclaimer, the term of this patent is extended or adjusted under 35 U.S.C. 154(b) by 111 days.

(21) Appl. No.: 11/404,405

(22) Filed: Apr. 14, 2006

(65) Prior Publication Data

US 2007/0238863 A1    Oct. 11, 2007

Related U.S. Application Data

(63) Continuation of application No. 09/857,539, filed as application No. PCT/US99/28793 on Dec. 7, 1999, now abandoned.

(60) Provisional application No. 60/111,225, filed on Dec. 7, 1998.

(51) Int. Cl.
*G01N 33/53* (2006.01)

(52) U.S. Cl. .................. 435/7.1; 435/70.2; 435/70.21; 435/7.92; 435/7.94; 435/7.95; 436/547; 436/548; 530/388.1; 530/388.6; 530/389.1; 530/822; 530/864; 424/130.1; 424/141.1; 424/151.1; 424/265.1; 424/543

(58) Field of Classification Search .................. 435/7.1, 435/70.2, 70.21, 7.92–7.95; 436/547, 548; 530/388.1, 388.6, 389.1, 822, 864; 424/130.1, 424/141.1, 151.1, 265.1, 543
See application file for complete search history.

(56) References Cited

FOREIGN PATENT DOCUMENTS

| WO | WO 97/36612 | * 10/1997 |
|----|-------------|-----------|
| WO | WO 98/07320 | * 2/1998  |

OTHER PUBLICATIONS

Petersen et al., Infection and Imunity, Dec. 1992. vol. 60, No. 12. pp. 5132-5138.*

(Continued)

*Primary Examiner*—Bao-Thuy L Nguyen
(74) *Attorney, Agent, or Firm*—Klarquist Sparkman, LLP

(57) ABSTRACT

A reagent and method for the specific and highly sensitive detection of *C. parvum* in which the reagent is an antibody for a soluble *C. parvum* sporozoite antigen and the method is an immunoassay in which the antibody is used to detect or quantify *C. parvum* sporozoite antigen in a sample. The sample is treated to cause excystation of *C. parvum* oocytes, thereby releasing a *C. parvum* sporozoite antigen, and combined with antibodies specific for the sporozoite antigen under conditions to form an antibody-antigen complex. Detection of the complex indicates the presence of *C. parvum* in the sample. The assay allows recognition and detection of *C. parvum* in turbid samples, and due to a lack of crossreactivity with other *Cryptosporidium* species, is specific for *C. parvum* contamination or infection. The assay is highly sensitive, allowing for the detection of less than 100 oocysts per milliliter of sample.

17 Claims, 6 Drawing Sheets

OTHER PUBLICATIONS

Figure 1:
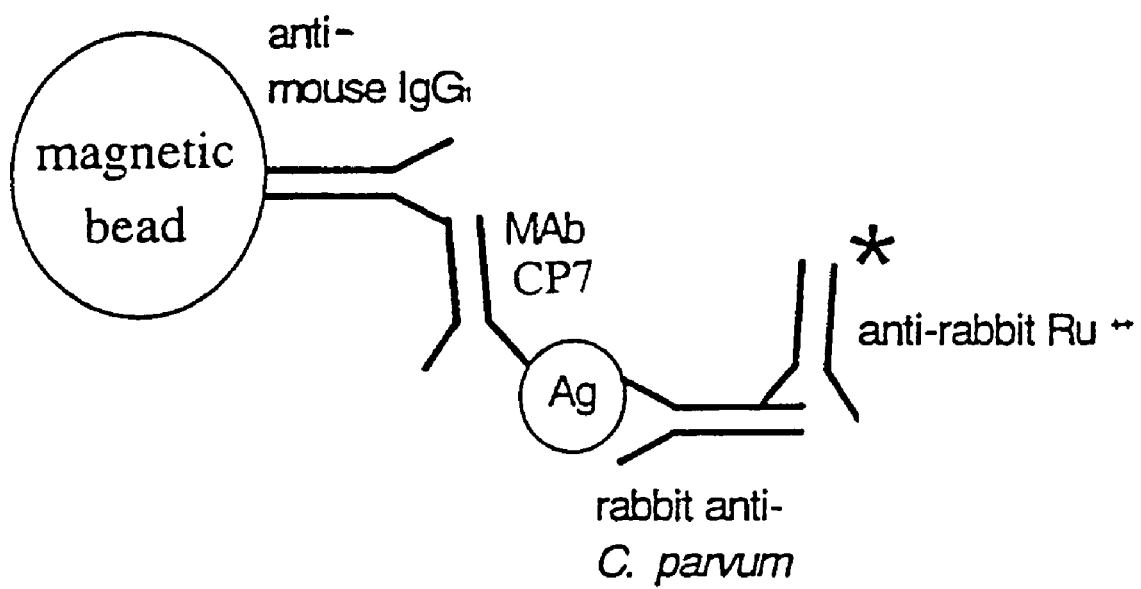

Barnes et al., "Novel Multi-Domain Mucin-Like Glycoprotein of *Cryptosporidium parvum* Mediates Invasion," *Molecular and Biochemical Parasitology*, 96:93-110, Oct. 30, 1998.

Cail et al., "Immunoassay For Viable *Crytosporidium parvum* Oocysts in Turbid Environmental Water Samples," *J. Parasitol*, 87(1):203-210, 2001.

Cevallos et al., "Mediation of *Cryptosporidium parvum* Infection In Vitro by Mucin-Like Glycoprotiens Defined by a Neutralizing Monoclonal Antibody," *Infection and Immunity*, 68(9):5167-5175, Sep. 2000.

Enriquez et al., "Role of immunoglobulin A monoclonal antibodies against p23 in controlling murin *Cryptosporidium parvum* infection," *Infection and Immunity*, 66(9):4469-4473, Sep. 1998.

Farrington et al., *Veterinary Parasitology*, vol. 60, No. 1-2, pp. 7-16, 1985.

Lee et al., "Development and Application of a Quantitative, Specific Assay for *Crytosporidium parvum* Oocyst Detection in High-Turbidity Environmental Water Samples," *Am. J. Med. Hyg.*, 65(1):1-9, 2001.

Moss et al., *Am. J. Trop. Med. Hyg.*, vol. 49, No. 3, pp. 393-401, 1993.

Petersen et al., "Identification and Initial Characterization of Five *Cryptosporidium parvum* Sporozoite Antigen Genes," *Infection and Immunity*, 60(6):2343-2348, Jun. 1992.

Petersen et al., *Infection and Immunity*, vol. 60, No. 12, pp. 5132-5138, 1992.

Riggs et al. "Neutralization-sensitive epitopes are exposed on the surface of infectious *Cryptosporidium parvum* sporozoites," *Journal of Immunology*, 143(4):1340-1345, Aug. 15, 1989.

Riggs et al., "Protective monoclonal antibody defines a cirmcumsporozoite-like glycoprotein exoantigen of *Cryptosporidium parvum* sporozoites and merozoites," *The Journal of Immunology*, Feb. 15, 1997, 158(4):1787-1795.

Tilley et al., *FEMS Microgiology Letters*, vol. 113, No. 2, pp. 235-240, 1993.

* cited by examiner

REAGENT AND METHOD FOR DETECTING A *CRYPTOSPORIDIUM PARVUM* SPOROZOITE ANTIGEN

This application is a continuation of, and claims priority to U.S. patent application Ser. No. 09/857,539, filed Jun. 6, 2001, which status is abandoned, which is a § 371 National Stage of PCT Application No. PCT/US99/28793, filed Dec. 7, 1999, which claims benifit of U.S. Provisional Application No. 60/111,225, filed Dec. 7, 1998, of which the entire contents of each are incorporated herein by reference.

This invention was made in the Centers for Disease Control. Therefore, the United States Government has certain rights in this invention.

FIELD OF THE INVENTION

The present invention relates to the field of immunology and more particularly to an immunoassay and reagent for detecting *Cryptosporidium parvum*.

BACKGROUND OF THE INVENTION

*Cryptosporidium parvum* (*C. parvum*) is a food or waterborne parasite that infects humans and animals causing severe intestinal distress. Infection caused by *C. parvum* is particularly dangerous because it can cause prolonged diarrheal illness that may be potentially fatal for immunocompromised individuals. Since the 1970s, *C. parvum* has been receiving increased world wide attention as the frequency of outbreaks and the number of individuals infected increase across the globe. For example, in an outbreak reported in Milwaukee, Wis. in 1993, approximately 400,000 people were infected with *C. parvum* and 50 premature deaths were attributed to the infection. Outbreaks have also been reported in Las Vegas, Nev.; London, England; and Australia. Therefore, the U.S. Environmental Protection Agency has begun the process of mandating that waters in the United States be tested for *Cryptosporidium*.

*C. parvum* oocysts are easily moved between watersheds by birds, and mammals, both domestic and wild. The remarkable resistance of oocysts to disinfectants, oocysts long-term environmental survival, and low infectious dose shows that conservative guidelines in detection and quality control of drinking water should be followed.

Although, cryptosporidiosis occurs worldwide, children, travelers to foreign countries, immunocompromised individuals and medical personnel caring for patients with the disease, are at particular risk. Apart from humans, *Cryptosporidium* infections are widespread in several other vertebrates including mammals, reptiles and fish. *Cryptosporidium parvum* in non-human mammals, but not reptiles or fish, is infectious to humans. Accordingly, the frequency of cryptosporidiosis in animal handlers and veterinarian personnel is reported to be relatively high.

Considerable efforts have been made to develop and improve *Cryptosporidium* detection methodologies through the application of a wide range of techniques such as flow cytometry, laser scanning, immunomagnetic separation, and polymerase chain reaction (PCR). However, the ability of existing detection methods to detect *C. parvum* in environmental samples has been limited due to factors such as interference caused by high sample turbidity and the inability to differentiate between viable and non-viable oocysts. Because the minimum infective dose is low (between 30-100 viable oocysts), the volume of sample to be analyzed is small, and the *Cryptosporidium* organism exists in several forms during its life cycle, detection methods must be highly sensitive or must utilize extensive sample concentration steps in order to be reliable.

The *C. parvum* life cycle is as follows: Oocysts enter the gastrointestinal system of the host, generally by the ingestion of contaminated food or water, and invade the intestinal and, very rarely, urogenital systems where the oocysts mature and release sporozoites. The sporozoites reproduce asexually to produce additional oocysts. These infective oocysts pass into the feces and are excreted. Following ingestion of the oocysts by another vertebrate, the oocysts release sporozoites that attach themselves to the epithelial surface of the gastrointestinal system and initiate a new cycle of infection by intercellular invasion.

As *C. parvum* organisms invade the surface of intestinal cells, the host experiences symptoms such as reduced appetite, severe diarrhea, abdominal cramping, and chronic fluid loss. The symptoms generally persist for five to eleven days, and then rapidly abate. However, in immunocompromised individuals, such as malnourished children, individuals with congenital hypogammaglobulinemia, those receiving immunosuppressants for cancer therapy or organ transplantation, and patients with AIDS, onset of the disease is more gradual and diarrhea is more severe, causing extreme fluid losses. Unless the underlying immunologic defect is corrected, the diarrhea may continue persistently or remittently for life because there is no effective, specific anti-*C. parvum* therapy available at present. Although some patients have responded positively to therapy with conventional antibiotics such as spiramycin and paromomycin, the result of infection is frequently fatal for immunocompromised individuals. In fact, cryptosporidiosis has been reported as one of the predominant causes of death in immunocompromised patients.

In light of the potentially fatal consequences of *C. parvum* infection, sensitive methods for detecting *C. parvum* contamination are necessary. In humans, the typical source of *C. parvum* is contaminated water, therefore the detection of *Cryptosporidium* in drinking and recreational water sources is a primary goal.

Currently available detection systems indicate that *C. parvum* organisms are observed in "spikes"; meaning that levels of *C. parvum* in samples collected upstream and downstream, from the same source of contamination, may not be identical when simultaneous readings are made. Consequently, *C. parvum* levels recorded from one location may differ significantly from readings taken from the same location minutes later. Detection of *C. parvum* in water is further complicated because the initial source of the infectious agent is difficult to identify. An abnormally high *C. parvum* concentration may be caused by water run-off from contaminated farm or pasture land, or an infected infant's soiled diaper carelessly discarded into a stream or worn in a public pool.

Ideally, continuous filtration systems having the capability to capture and retain *C. parvum* organisms for subsequent analysis would be installed in all water supply reservoirs to allow for continuous monitoring. Unfortunately, filtration systems currently in use often have filtration cartridges that either fail to retain organisms, frequently become clogged with mud or sediment, or must be replaced or cleaned with a frequency that renders the cartridges impractical.

*C. parvum* detection assays presently in use are cumbersome and frequently inaccurate. For example, most assay test samples begin as crude mixtures of *C. parvum* oocysts separated out from mud deposits collected by filters. The oocysts are isolated by processes involving centrifugation and ultrafiltration. Separating oocysts in this manner is often tedious and inefficient since each time the test sample is spun and filtered, oocysts are lost in the process, inevitably resulting in a lack of sensitivity and related inaccuracies. Another significant disadvantage of such assays is the large amount of time required for processing test samples. For example, in order to improve the optical properties of test samples for detection, oocysts must be stained. Typically, staining and subsequent detection procedures can take up to four days. Furthermore, samples can be tested only in small increments, and the sensitivity of most currently available assays is very low. Generally at least 50,000 C. parvum oocysts per milliliter must be present for a positive detection result. However, the minimum infective dose is low, between 30 and 100 oocysts. Therefore, C. parvum assays currently in use are generally inefficient, inaccurate and inconsistent.

Another barrier to effective Cryptosporidium screening concerns sample turbidity. The term "turbidity" refers specifically to the clarity or transparency of water and the effect that any suspended particles in the water may have on this clarity. Turbidity is determined by quantifying the amount of light allowed to pass through a sample and is measured in NTUs (nephelometric turbidity units). Many source water sites of public water reservoirs (e.g., rivers and lakes) often have turbidities up to 100 NTUs, whereas finished water (e.g., reservoirs for public consumption) tend to have turbidities in the range of 0 to 5 NTUs. High turbidities are defined herein as having greater than 10 NTUs.

Because it is commonly suspected that Cryptosporidium contamination occurs at source water sites, efforts have been focused on assaying samples at reservoir intakes. Several liters of source water are pumped through filters that are rated to capture particles the size of oocysts or larger. Pumping source water in this way causes large amounts of sediment to obstruct the flow of water through filters and therefore limit the volume of water passing through the filters. The filter retentates are then eluted and assayed for the presence of microorganisms. These retentates can have turbidities up to 300,000 NTU and yield highly variable C. parvum oocyst counts by immunofluorescence assay due to the loss of oocysts that occurs in multi-step sample processing. Concentrations of the retentates can increase turbidities further.

Oocysts present in filter eluate often tend to be washed away during processing and therefore go undetected in the final step of detection assays. Consequently, currently available methods such as immunofluorescence assays (IFA) and enzyme immunoassays (EIA), are mainly useful for detecting oocysts in "clean" samples (i.e., samples that have low turbidity). Such assays are more likely to give reproducible results with clean samples than those that are considered "dirty" (i.e., samples that have high turbidity).

Currently available Cryptosporidium detection methods for public health surveillance of oocyst exposure are incapable of distinguishing C. parvum from other Cryptosporidium species. In addition, current detection methods count the total number of oocysts in the sample, without regard for viability; therefore, both viable and non-viable oocysts are counted. Oocyst viability, measured by the ability of an oocyst to excyst, is valuable because over time, oocysts lose the ability to excyst and thus become noninfective. Therefore, any attempted correlation between the number of oocysts in drinking water and the incidence and risk for disease in healthy and immunocompromised persons is unreliable.

Clinical diagnosis of cryptosporidiosis is made by recovering acid-fast oocysts from stool samples. Excretion of acid-fast oocysts is most intense during the first four days of illness but persists for the duration of diarrhea. Other assays currently in use for diagnostic purposes involve the use of formalin-ethyl acetate sedimentation or Sheather's sugar flotation stool concentration procedure to enhance the yield of oocysts in specimens containing few oocysts. Commercial fluorescein-labeled monoclonal antibody kits also provide detection of oocysts in clinical specimens. (Merck Manual, Chapter 15 pp. 237-238 16th ed. (1992)). The disadvantage of such clinical tests is that, depending on the stage of *C. parvum* infection, the assays may or may not be adequately sensitive for detecting oocysts. In addition, such clinical tests generally involve a multitude of steps thereby introducing a greater likelihood of inaccuracies. Furthermore, no "standard" for testing stool specimens for *C. parvum* has been established, and so the absolute sensitivity of currently used methods has not been assessed. (Christine L. Roberts et al., JOURN. OF CLIN. MICRO., Vol. 34 No. 9, pp. 2292-2293 (1996)). Other problems associated with *C. parvum* testing include extensive processing time and low test positivity rates.

In summary, existing assays for *C. parvum* parasites are irreproducible, non-specific, insensitive, labor-intensive, susceptible to interference by sample turbidity, and time consuming. In addition, existing assays are not quantitative, lack the ability to distinguish different species of *Cryptosporidium* or distinguish infectious from non-infectious organisms, and are unable to correlate parasite levels in drinking water with incidence and severity of disease. Useful assays that enable correlation of disease-parasite levels are required for the development of environmental guidelines for safeguarding water sources against *C. parvum* and other parasitic infestation.

What is needed, therefore, is a sensitive, quantitative and reproducible assay for *C. parvum.*

SUMMARY OF THE INVENTION

An efficient and sensitive method and reagent for the detection of *C. parvum*, is provided. The reagent is an antibody having binding specificity for a soluble *C. parvum* sporozoite antigen. In accordance with the method, a sample is treated to excyst *C. parvum* oocysts, thereby releasing a sporozoite antigen, and combined with antibodies specific for the sporozoite antigen under conditions to form an antibody-antigen complex. Detection of the complex indicates the presence of *C. parvum* oocysts in the sample, particularly viable or excystable *C. parvum* oocysts. The assay allows recognition and detection of viable or excystable *C. parvum* in turbid samples, distinguishes *C. parvum* from other *Cryptosporidium* species, and provides an indication of the infectivity risk of the sample.

The assay is especially useful for detecting *C. parvum* oocysts present in water such as recreational water, natural bodies of water, finished or treated water such as community water reservoirs, and biological fluid samples. The assay is highly sensitive, allowing for the detection of less than 200 oocysts per milliliter, preferably less than 100 oocysts per milliliter.

The assay is particularly suited for *C. parvum* detection in environmental water and biological fluid samples because it can operate in both low and high turbidity samples, has high reproducibility, and can be performed with little sample manipulation or processing.

In a first preferred embodiment of the immunoassay, the oocysts are treated to cause excystation by biological mechanisms. Therefore, only sporozoites from viable oocysts are released, and the results of the immunoassay provide an indication of the presence or amount of infectious *C. parvum* in the sample.

In a second preferred embodiment of the immunoassay, the oocysts are mechanically disrupted, such as by freezing and thawing the sample or by sonication. Therefore, the sporozoites from both viable and non-viable oocysts are released, and the results provide an indication of the total concentration of oocysts in the sample, without regard to infectivity.

Accordingly, it is an object of the present invention to provide a qualitative or quantitative assay for the detection C. parvum oocysts in a sample that is highly sensitive, simple to perform, rapid, and does not require extensive sample manipulation, such as sample purification, centrifugation or concentration.

It is yet another object of the present invention to provide a detection assay capable of detecting viable C. parvum oocysts in turbid samples, particularly turbid water samples, biological fluid samples and fecal samples.

Another object of the present invention is to provide a quantitative detection assay enabling the correlation of C. parvum oocyst levels and the incidence of disease.

Another object of the present invention is to provide an antibody to C. parvum that is specific for viable C. parvum oocysts and does not crossreact with other Cryptosporidium species.

Another object of the present invention is to provide a kit for automated point-of-use analysis for detecting C. parvum in water or biological fluid samples.

Another object of the present invention is to provide a method for detecting C. parvum that does not utilize a microscope.

Another object of the present invention is to provide a method for detecting *C. parvum* that is specific for the species of *C. parvum* that infects mammals.

Another object of the present invention is to provide an immunoassay for *C. parvum* that utilizes electrochemiluminescence (ECL) technology.

These and other objects, features and advantages of the present invention will become apparent after a review of the following detailed description of the disclosed embodiments and the appended claims.

BRIEF DESCRIPTION OF THE FIGURES

FIG. 1 is a schematic diagram of a detectable antibody-antigen complex containing the anti-*C. parvum* sporozoite antigen monoclonal antibody described herein bound to solubilized *C. parvum* sporozoite antigen.

FIG. 2 is a graph showing freeze/thawed ECL signal/4° C. ECL background versus oocyst number in three lake samples and $dH_2O$ in which the titrated oocysts have been freeze/thawed as determined using the immunoassay method described herein. The open circle symbol is lake A (3125 NTUs), the closed triangle symbol is lake B (90 NTUs), the closed circle symbol is lake C (107 NTUs) and the open triangle symbol is $dH_2O$.

FIG. 3 is a graph showing freeze/thawed ECL signal/4° C. ECL background versus oocyst number in three lake samples and $dH_2O$ in which the titrated oocysts have been excysted as determined using the immunoassay method described herein. The open circle symbol is lake A (3125 NTUs), the closed triangle symbol is lake B (90 NTUs), the closed circle symbol is lake C (107 NTUs) and the open triangle symbol is $dH_2O$.

FIG. 4 is a bar graph showing electrochemiluminescent counts for *C. parvum* and six other parasites measured using the immunoassay described herein, demonstrating that the assay is specific for *C. parvum* and does not cross-react with the other parasites.

FIG. 5 is a bar graph showing the titration of NTUs in two environmental samples and dH20 in which the titrated oocysts have been excysted as determined using the immunoassay method described herein.

FIG. 6 is a graph showing freeze/thawed ECL signal/4° C. ECL background versus oocyst number in one lake sample and $dH_2O$ in which the titrated oocysts have been excysted as determined using the immunoassay method described herein.

DETAILED DESCRIPTION

A reagent and method for the specific and highly sensitive detection of *C. parvum* are described herein. The reagent is an antibody having binding specificity for a soluble *C. parvum* sporozoite antigen. Both monoclonal and polyclonal antibodies are described. The method is an immunoassay in which the antibody is used to capture or detect *C. parvum* sporozoite antigen.

In accordance with the method, a sample is treated to cause excystation of *C. parvum* oocysts, thereby releasing a *C. parvum* sporozoite antigen, and combined with antibodies specific for the sporozoite antigen under conditions to form an antibody-antigen complex. Detection of the complex indicates the presence of viable *C. parvum* in the sample. The assay allows recognition and detection of viable *C. parvum* in turbid samples, and due to a lack of crossreactivity with other *Cryptosporidium* species, is specific for *C. parvum* contamination or infection. The assay is highly sensitive, allowing for the detection of less than 100 oocysts per milliliter.

The reagent and assay are especially useful for detecting viable *C. parvum* oocysts present in water samples including, but not limited to, recreational water such as swimming pools, natural bodies of water such as lakes and streams, and finished or treated water such as community water reservoirs, so that contaminated water may be treated or quarantined as needed to prevent human or animal exposure and infection. The reagent and assay are also useful for diagnosing or monitoring *C. parvum* infection in humans or animals by detecting viable *C. parvum* oocysts in biological samples such as biological fluid samples.

The assay is particularly suited for *C. parvum* detection in environmental water and biological fluid samples because it can operate in both low and high turbidity samples, has high reproducibility, and can be performed with little sample manipulation or processing.

In a first preferred embodiment of the immunoassay, the oocysts are treated to cause excystation by biological mechanisms. Therefore, only sporozoites from viable oocysts are released, and the results of the immunoassay provide an indication of the presence or amount of infectious *C. parvum* in the sample.

In a second preferred embodiment of the immunoassay, the oocysts are mechanically disrupted, such as by freezing and thawing the sample. Therefore, the sporozoites from both viable and non-viable oocysts are released, and the results provide an indication of the total concentration of oocysts in the sample, without regard to infectivity.

Definitions

The terms "a", "an" and "the" as used herein are defined to mean "one or more" and include the plural unless the context is inappropriate.

The terms "detecting" or "detected" as used herein mean using known techniques for detection of biologic molecules such as immunochemical or histological methods and refer to qualitatively or quantitatively determining the presence or concentration of the biomolecule under investigation.

By "isolated" is meant a biological molecule free from at least some of the components with which it naturally occurs.

The terms "antibody" or "antibodies" as used herein include monoclonal antibodies, polyclonal, chimeric, single chain, bispecific, simianized, and humanized antibodies as well as Fab fragments, including the products of an Fab immunoglobulin expression library.

As used herein, the term "soluble" means partially or completely dissolved in an aqueous solution.

Sporozoite Antigen Antibodies

The antibody provided herein is a monoclonal or polyclonal antibody having binding specificity for a soluble *C. parvum* sporozoite antigen. The preferred antibody is a monoclonal antibody, due to its higher specificity for analyte. The antibody exhibits minimal or no crossreactivity with oocyst proteins or peptides. Preferably, the antibody is specific for an antigen, such as a membrane-bound protein or glycoprotein. The antibody is specific for *C. parvum* and exhibits minimal or no crossreactive binding to other *Cryptosporidium* species such as, but not limited to, *C. baileyi, C. muris, C. serpentis*, or other protozoan pathogens such as *Giardia duodenalis, Eimeria papillate*, or *E. nieschulzi.*

The monoclonal antibody is prepared by immunizing an animal, such as a mouse or rabbit, with a whole sporozoite homogenate containing one or more soluble sporozoite antigens. The homogenate is prepared by biologically existing *C. parvum* oocysts, preferably by incubation in cell culture media at a temperature greater than room temperature for a sufficient amount of time to cause the oocyst to fracture, thereby releasing sporozoites. The sporozoite suspension is separated from oocyst cell wall debris by filtration, preferably by passage through a 1 to 5 μm filter, and centrifugation. The filtrate is then combined with an adjuvant, such as Freund's Complete or Incomplete Adjuvant or a buffered solution, such as phosphate buffered saline, and multiple boost inoculations are administered to the animal over a period of time to ensure an effective immune response and the production of antibodies. Alternatively, the animal is immunized with an isolated, soluble sporozoite antigen to produce antibodies specific for that particular antigen.

Spleen cells are harvested from the immunized animals and hybridomas generated by fusing sensitized spleen cells with a myeloma cell line, such as murine SP2/O myeloma cells (ATCC, Manassas, Va.). The cells are induced to fuse by the addition of polyethylene glycol. Hybridomas are chemically selected by plating the cells in a selection medium containing hypoxanthine, aminopterin and thymidine (HAT).

Hybridomas are subsequently screened for the ability to produce monoclonal antibodies against sporozoite antigens and oocyst cell wall antigens. Sporozoite antigens used for screening purposes are obtained from excysted, purified sporozoites that have been homogenized and treated with proteolytic enzyme inhibitors, such as Pepstatin A™, Leupeptin™ and Pefablock™ enzymes. Oocyst cell wall antigens are obtained from the debris retained on the filter through which the sporozoite suspension was passed as described above.

Hybridomas producing antibodies that bind to the sporozoite antigen preparation and preferably also bind to intact sporozoites, but do not bind to oocyst cell wall antigens, are cloned, expanded and stored frozen for future production. The preferred hybridoma produces a monoclonal antibody having the IgG isotype, more preferably the IgG1 isotype. Most preferably, the preferred hybridoma is the hybridoma deposited on Dec. 1, 1998 under the Budapest Treat with the American Type Culture Collection (ATCC, 10801 University Blvd., Manassas, Va. 20110-2209) under ATCC Accession No. CRL-12604, that produces the monoclonal antibody referred to herein as CP7.

The polyclonal antibody is prepared by immunizing animals, such as mice or rabbits with the sporozoite antigen homogenates described above or with whole oocyst antigens, as follows. Blood sera is subsequently collected from the animals, and antibodies in the sera screened for binding reactivity against the soluble sporozoite antigens, preferably the antigens that are reactive with the monoclonal antibody described above, most preferably the monoclonal antibody CP7.

In a first preferred embodiment, polyclonal antibodies are prepared by immunizing animals with homogenates of oocysts that have been excysted using biological mechanisms to release sporozoites from viable oocysts. In a second preferred embodiment, polyclonal antibodies are prepared by immunizing animals with homogenates of oocysts that have been excysted using mechanical disruption, such as freezing and thawing, thereby releasing sporozoite antigens from both viable and non-viable *C. parvum* organisms.

Either the monoclonal antibody or the polyclonal antibody, or both may be labeled directly with a detectable label for identification and quantitation of *C. parvum* in a biological or environmental sample as described below. Labels for use in immunoassays are generally known to those skilled in the art and include enzymes, radioisotopes, and fluorescent, luminescent and chromogenic substances including colored particles, such as colloidal gold and latex beads. The antibodies may also be bound to a solid phase to facilitate separation of antibody-antigen complexes from non-reacted components in an immunoassay. Exemplary solid phase substances include, but are not limited to, microtiter plates, test tubes, magnetic, plastic or glass beads and slides. Methods for coupling antibodies to solid phases are well known to those skilled in the art.

Alternatively, the antibody may be labeled indirectly by reaction with labeled substances that have an affinity for immunoglobulin, such as protein A or G or second antibodies. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

In a preferred embodiment, the antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the monoclonal antibody to be used in the assay described below, this label is preferably an antibody-coated bead, particularly a magnetic bead. For the polyclonal antibody to be employed in the immunoassay described herein, the label is preferably a detectable molecule such as a radioactive, fluorescent or an electrochemiluminescent substance, such as a ruthenium ($Ru^{++}$) label.

*C. Parvum* Immunoassay

A highly sensitive *C. parvum* immunoassay employing one or more of the antibodies described above is provided. The immunoassay is useful for detecting the presence or amount of *C. parvum* infection in a variety of samples, particularly environmental samples, such as contaminated water, and biological samples, such as human or animal biological fluids or feces. The sample may be obtained from any source in which the *C. parvum* organism may exist. For example, the sample may include, but is not limited to, water from lakes, rivers, streams, ponds, and wetlands; recreational water; treated water from water treatment plants; commercial effluent; and the like.

In a first preferred embodiment, the immunoassay is designed to detect the presence or concentration of viable *C. parvum* oocysts in a sample. This is achieved by first treating the sample to cause excystation of oocysts in the sample, using biological mechanisms. An exemplary mechanism is incubation at a temperature above room temperature, preferably approximately 30-45° C. for approximately 30 to 150 minutes, more preferably approximately 37° C. for 60 minutes in the dark. The results of this immunoassay provide a direct indication of the infectivity risk of the source from which the sample was removed.

In a second preferred embodiment, the immunoassay detects the presence or concentration of viable and nonviable *C. parvum* oocysts in the sample. In this design, the sample is treated in such a way that oocysts are mechanically disrupted, such as by freezing and thawing, to liberate sporozoites from both viable and nonviable oocysts, thus indicating the total number of oocysts in the sample.

It will be understood by those skilled in the art that one or more of the antibodies described above may be employed in any heterogenous or homogenous, competitive immunoassay for the detection of *C. parvum*. As mentioned above, for use in the immunoassay provided herein, the antibody is labeled with a detectable label or coupled to a solid phase. Preferably, both a monoclonal antibody and a polyclonal antibody are used in the assay, with the monoclonal antibody indirectly coupled to a solid phase and the polyclonal antibody indirectly labeled with a detectable label as shown schematically in FIG. 1. The preferred solid phase is a commercially available magnetic bead, such as one of the paramagnetic beads available from Dynal (New York, N.Y.). The preferred detectable label is an electrochemiluminescent label. Preferably the monoclonal antibody is the antibody referred to herein as CP7, which is produced by the hybridoma deposited under the Budapest Treaty with the American Type Culture Collection (ATCC, 10801 University Blvd., Manassas, Va. 20110-2209).

In accordance with the preferred method, the sample and the antibody bound to a solid phase are reacted together for a sufficient amount of time under conditions that promote the binding of antibody to soluble sporozoite antigen in the sample. It will be understood by those skilled in the art that the immunoassay reagents and sample may be reacted in different combinations and orders. A physical means is employed to separate reagents bound to the solid phase from unbound reagents such as filtration of particles, decantation of reaction solutions from coated tubes or wells, magnetic separation, capillary action, and other means known to those skilled in the art. It will also be understood that a separate washing of the solid phase may be included in the method.

The antibody-antigen complexes formed in the immunoassay are detected using immunoassay methods known to those skilled in the art, including sandwich immunoassays and competitive immunoassays. The antibody-antigen complexes are exposed to antibodies similar to those used to capture the antigen, but which have been labeled with a detectable label. Suitable labels include: chemiluminescent labels, such as horseradish peroxidase; electrochemiluminescent labels, such as ruthenium and aequorin; bioluminescent labels, such as luciferase; fluorescent labels such as FITC; and enzymatic labels such as alkaline phosphatase, β-galactosidase, and horseradish peroxidase. Preferably, the label is detected by electrochemiluminescence. Most preferably, the detecting antibody is modified by the addition of a ruthenium ($Ru^{++}$) label.

The labeled complex is then detected using a detection technique or instrument specific for detection of the label employed. Preferably, the complexes are analyzed by an electrochemiluminescence instrument such as the ORIGEN™ ANALYZER (Igen, Inc., Gaithersburg, Md.) for $Ru^{++}$ photon emission. Soluble antigen or antigens may also be incubated with magnetic beads coated with non-specific antibodies in an identical assay format to determine the background values of samples analyzed in the assay.

In a preferred embodiment of the present method, solubilized antigen is complexed with monoclonal antibody-coated magnetic beads, and the beads are captured by an electromagnet present in the flow cell of the ORIGEN™ ANALYZER. After capture, the $Ru^{++}$ present in immunocomplexes is triggered to release a photon of light by the addition of the electron donor tripropylamine followed by the application of an electrical field. Light measured by a photomultiplier tube is then expressed in electrochemiluminescent (ECL) counts. Samples positive for the parasite, such as *C. parvum*, will yield ECL counts above a set background signal.

The preferred assay approach is to immunologically target a soluble antigen which is indicative of excystation. By using a capture immunoassay format, the target antigen is easily separated from nonreacted components and organism debris, thus eliminating the need for further sample manipulation, such as oocyst purification, thereby avoiding significant losses of oocysts. By choosing a sporozoite-specific antigen as the target, the immunoassay is capable of differentiating low numbers of viable (excystable) *C. parvum* oocysts from non-viable (non-excystable) oocysts in difficult samples, such as turbid environmental samples.

The preferred assay utilizes a monoclonal antibody to capture a sporozoite antigen, and the captured antigen is then detected by a labeled polyclonal antibody. A more preferred assay configuration uses an isotype-specific antibody-coated magnetic bead to capture an anti-*C. parvum* monoclonal antibody, the bead-monoclonal antibody complex is then transferred to and incubated with the sample. After antigen in the sample has been captured and washed of unbound material, the antigen is then reacted with polyclonal anti-*C. parvum* sera. The bound polyclonal antibody is then detected, preferably with a electrochemiluminescent-labeled isotype-specific polyclonal antibody, the electrochemiluminescence (ECL) excitation is then detected using an electrochemiluminescence detector as described above.

Assay Characteristics

The immunoassay provided herein allows for the differentiation of viable from nonviable *C. parvum* oocysts in a sample, thereby permitting a realistic indication of the infectivity risk posed by the source from which the sample is removed.

The detection assay described herein is efficient because of the rapid rate at which samples may be screened, processed and analyzed. Typically, samples of approximately 1 ml may be analyzed within several hours. Much of this time is the excystation procedure and subsequent antigen capture incubations and requires little or no manual manipulation from a laboratory technician. In addition, the assay has improved efficiency due to the higher recovery of C. parvum oocysts as a result of limited sample processing.

The immunoassay is a rapid and quantitative assay that is not adversely affected by test sample turbidity. The assay time of the present invention for detecting C. parvum oocysts in source or finished water and in fecal sample is approximately six hours, while the existing microscopic assays for this organism in water samples can take up to four days to complete.

Figure 3:
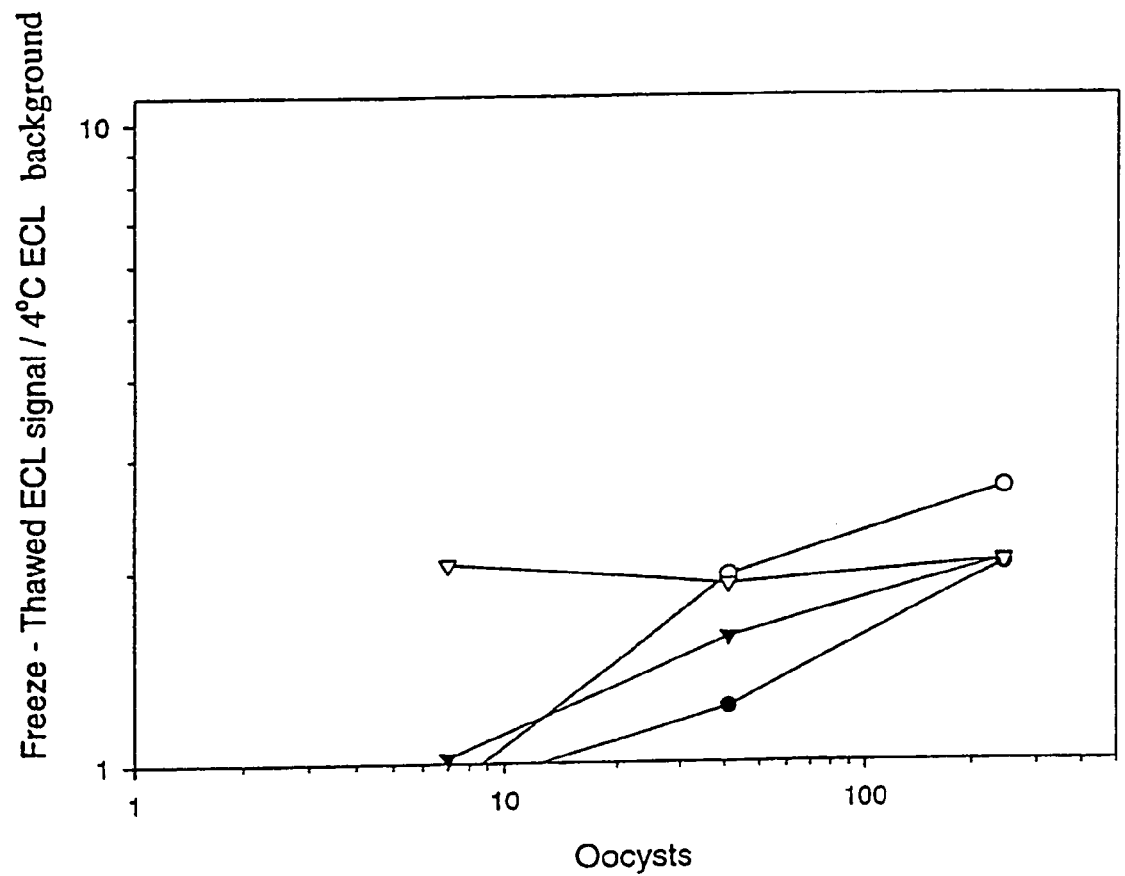

The method described herein can successfully detect C. parvum oocysts in one milliliter samples containing less than 200 oocysts in turbid environmental water samples containing in excess of 3,000 NTUs, and can preferably detect as few as 100 oocysts/ml. Most preferably, the method can successfully detect 80 oocysts/ml or less as shown in FIG. 3. This is a significant improvement over the sensitivity of presently available methods that fail to detect C. parvum in one milliliter samples containing up to 50,000 oocysts.

Figure 4:
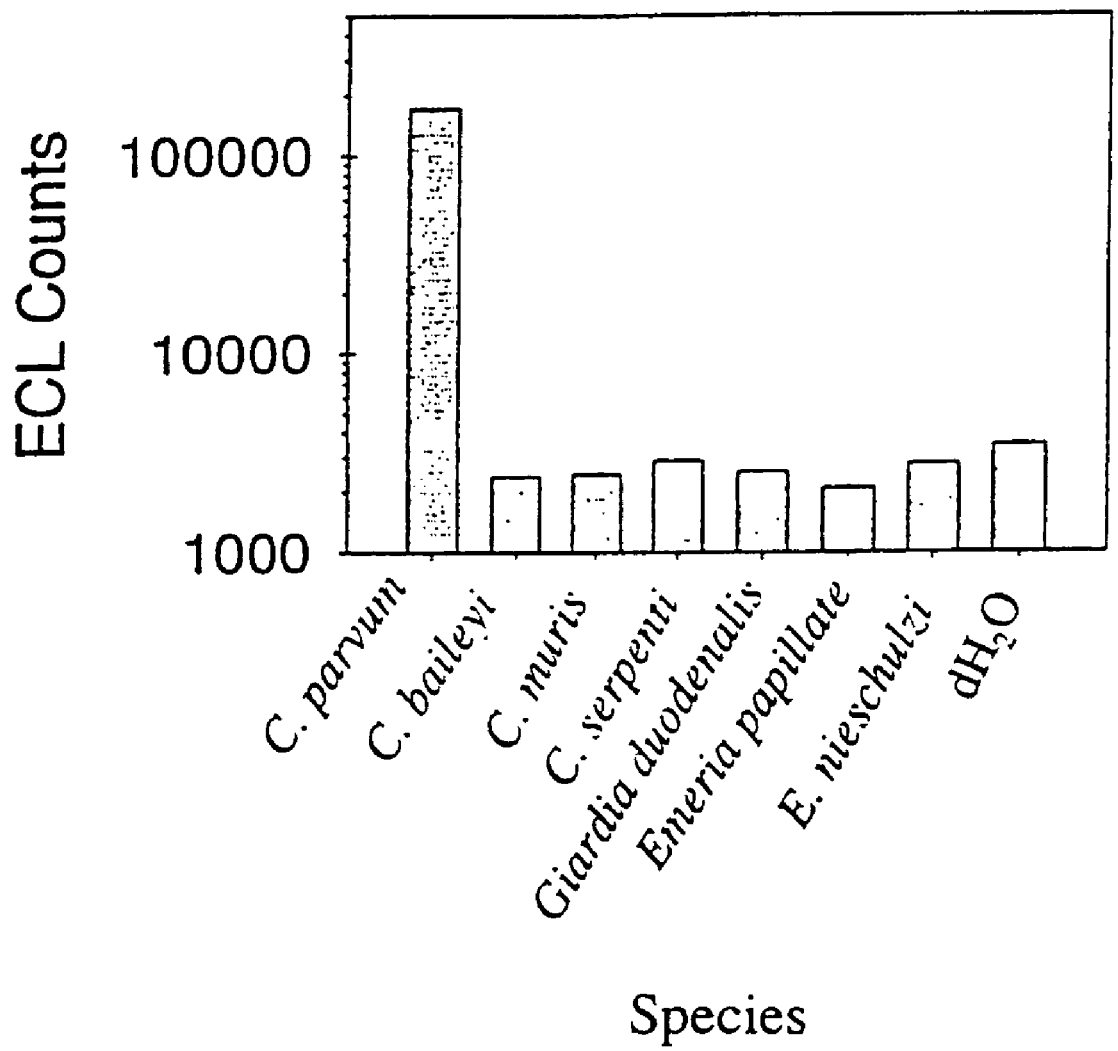
Figure 5:
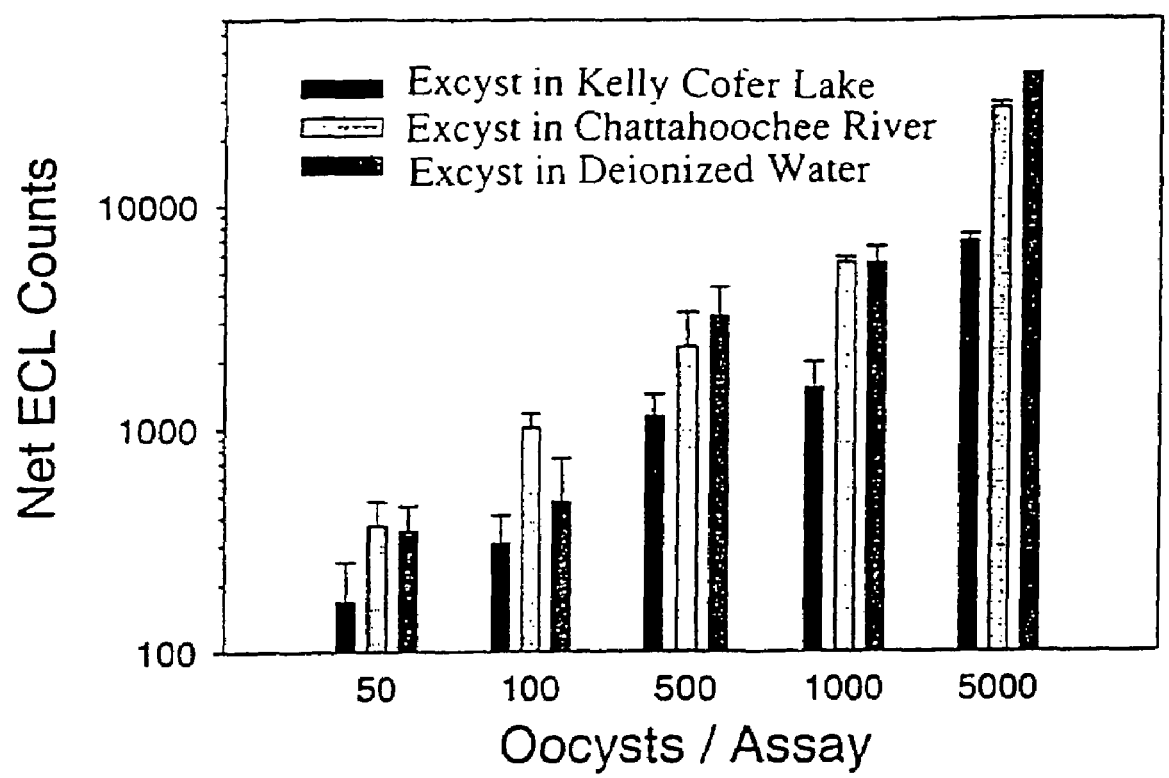
Figure 6:
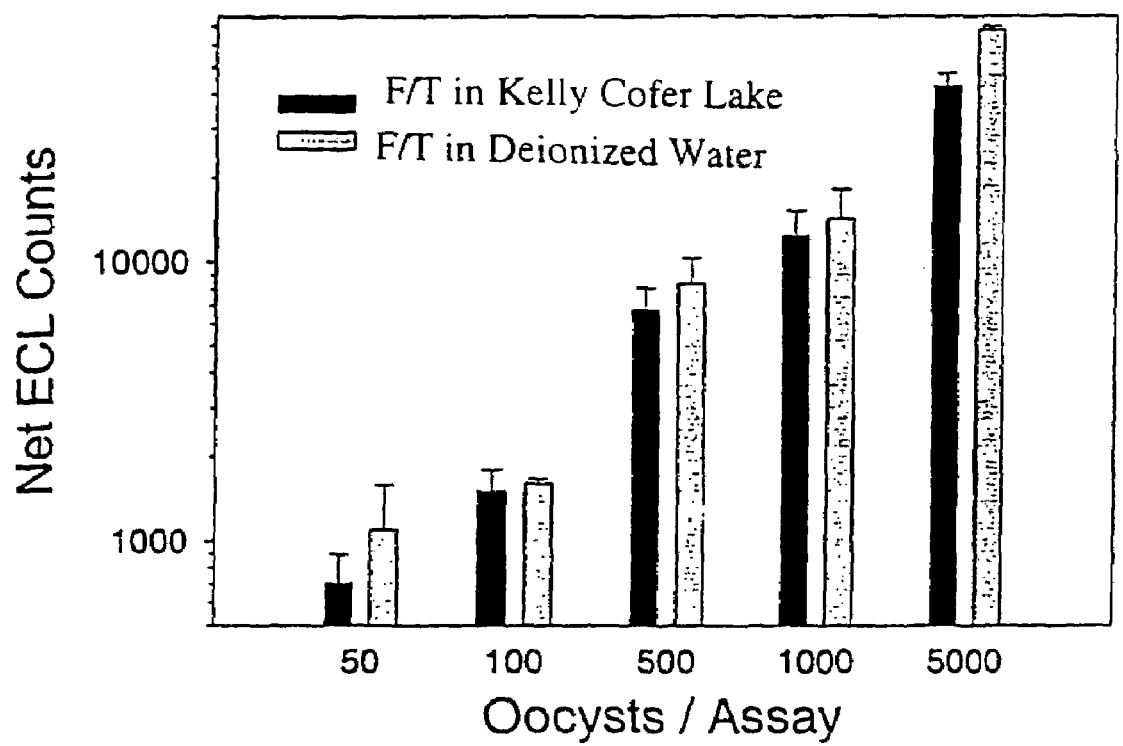

As shown in FIG. 3, the assay is not subject to interference by sample turbidities and can properly process samples having up to 3,000 NTUs or more. In comparison, current methodologies such as immunofluorescence assays (IFA) and enzyme immunoassays (EIA) are time consuming and severely limited by sample turbidity. Since sample turbidity is not a major impairment to successful detection by the method described herein, the assay is suitable for detecting oocysts in samples of source or finished water filtrate obtained from the eluate of filter cartridges (which commonly exhibit turbidities as high as approximately 300,000 NTUs or more if the sample is concentrated). Furthermore, as demonstrated by FIG. 4, the assay is specific for C. parvum: in that it exhibits minimal or no cross-reactivity with other species of Cryptosporidium or other protozoal pathogens. In addition, the assay detects both human and zoonotic isolates of C. parvum.

The assay is also valuable for epidemiological reasons as it may be used to identify low-level infections in patients. This is especially important because existing assays for C. parvum have low sensitivity making the detection of asymptomatic cryptosporidiosis a formidable task. Unlike the assay described herein, presently available assays are generally considered inaccurate and inefficient due to the variation in consistency between individual samples, the variation in amount of specimen used, and oocyst losses incurred during laborious sample preparation.

Unlike assays currently used in the art, the presently described method detects C. parvum by recognition of an antigen of the organism. The advantage of this type of recognition is that the assay is neither dependent upon recognizing the parasite in particulate form or upon detecting the presence of oocysts that are intact. Instead the assay is directed at detecting the presence of soluble antigens that are present in abundance in the sporozoite. Detection based on the presence of soluble antigen both increases the sensitivity of the method, and reduces interference resulting from sample turbidity.

Figure 2:
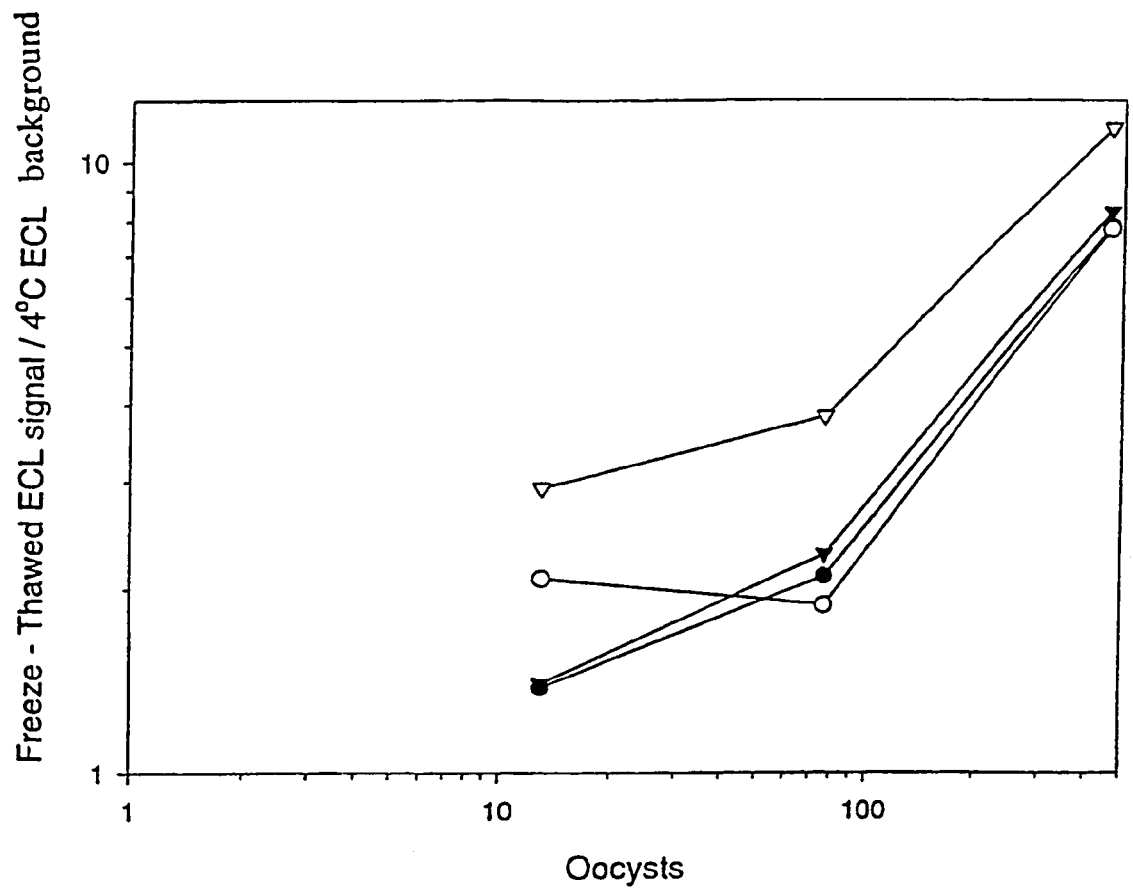

As indicated in FIGS. 2 and 3, (titration of oocysts) the ECL counts derived from the immunoassay described herein, exhibit a linear relationship with the number of oocysts within the range of the assay sensitivity. This linear relationship allows for this assay to be used in a quantifiable manner for those studies in which oocyst viability is to be measured. The assay is not only of use in laboratories concerned with the detection of protozoa in water but is also a valuable tool in further research into the conditions which affect the excystation of oocysts.

While sensitive detection methods are important, equal consideration must be given to sample concentration methodology. Using retention filtration as a method of concentration, it is difficult to separate oocysts from the debris of environmental samples without losing a large number of oocysts. Concentration techniques that are compatible with viability determination assays and suitable for rapid processing of large sample volumes are of great importance. Because the immunoassay described herein is compatible within a very wide range of turbidities (NTUs), it is possible to use retention filtration techniques in this assay. In addition, immunoassay targets a soluble antigen, thus opening up the possibility of excystion of target antigen without recovery of whole oocysts from the filter matrix, a recognized problem of retention filter technology.

The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Preparation of C. Parvum Antibodies

Antibodies having binding specificities for C. parvum soluble sporozoite antigens are prepared as follows:

Cryptosporidium parvum oocysts used for polyclonal and monoclonal antibody production were propagated in newborn Holstein (Bos. tauris) calves at the Centers for Disease Control and Prevention, Lawrenceville, Ga. (Iowa bovine isolate, originally obtained from Dr. Harley Moon, (National Animal Disease Center, Ames, Iowa). These oocysts were purified from feces using discontinuous sucrose and cesium chloride gradients, and stored at 4° C. in 2.5% potassium dichromate until used as taught by Arrowood and Sterling, *J. Parasitol*. 73:314-319 (1987) and Arrowood and Donaldson, *J. Parasitol*. 81(3):404-409 (1996). The concentration of the oocyst suspension was determined in triplicate with a hemocytometer.

*Cryptosporidium parvum* oocysts (Iowa bovine isolate) used for the excystation assay development were obtained from Pat Mason (Sunny Brooke Farms, Tracy, Id.), and isolated using methods described by Riggs and Perryman, *Infect. Immun*. 56(2)537 (1988). For the viability assay, the diethyl ether extraction method was used for the isolation of the *C. parvum* oocysts. Purified oocysts were stored at 4° C. in phosphate buffered saline (PBS) with 100 U penicillin G sodium $ml^{-1}$ and 100 μg streptomycin sulfate $ml^{-1}$. The concentration of the oocyst suspension was determined in triplicate with a hemocytometer, and adjusted to $2\times10^7$ $ml^{-1}$ in the PBS antibiotic suspension.

Monoclonal Antibody Production: Antigen Preparation

The monoclonal antibody used for antigen capture was made by immunizing mice with a whole sporozoite homogenate. Sporozoites were excysted and separated from oocyst wall fragments using the previously described method of Arrowood, et al., (*J. Eukaryotic Microbiol*. 41(5):23S 1994). In brief, with the main substitution being the lack of fluorescence labeling, $5\times10^6$ purified fresh oocysts, 4 to 8 weeks old, were washed, treated with sodium periodate, and blocked with PBS/BSA (PBS with 0.1% bovine serum albumin). After the sodium periodate oxidation, oocysts were washed and resuspended into 1 ml of 0.75% sodium taurocholate (Sigma Chemical Company, St. Louis, Mo.). In cell culture media, sporozoites were excysted at 37° C. for 60 minutes in the dark. The excysted oocyst suspension was drawn into a sterile 1 ml syringe using a 23 gauge needle, passed through a 3 µm MicroPrep™ polycarbonate track etch PCTE™ syringe filter (Poretics Corp., Livermore, Calif.), and collected into a 1.5 ml microfuge tube. The excysted separated sporozoites were washed with PBS by centrifugation, and the sporozoite pellet was resuspended into 4.0 ml of PBS. One ml of the sporozoite suspension was mixed 1:1 with Freund's Complete Adjuvant (FCA) and homogenized with a microtip homogenizer. The remaining sporozoite suspension was mixed 1:1 with Freund's Incomplete Adjuvant (FIA) and homogenized in the same way.

The immunizing sporozoite antigen/FIA was frozen at −70° C., and thawed just prior to each boost at weeks 2, 5, and 8. At week 12, freshly prepared sporozoites from $1 \times 10^6$ oocysts were excysted, and separated from oocyst walls. They were then homogenized in PBS only and used as the final immunogen prior to fusion.

Mouse B-Cell Fusions

Spleens from the immunized mice were harvested 4 days after a final 200 µl intraperitoneal injection of homogenized sporozoites in PBS without adjuvant. Hybridomas were generated by fusing sensitized spleen cells with murine SP2/O myeloma cells and using polyethylene glycol (PEG) 1400 (Kodak, Rochester, N.Y.), as described by the American Type Culture Collection (1993).

After selection in hypoxanthine-aminopterin-thymidine (HAT) medium, hybridomas were screened for antibody production against sporozoite and oocyst wall antigens. Sporozoite antigens were obtained from excysted, purified sporozoites, homogenized in PBS with proteolytic enzyme inhibitors added (Pepstatin A™ enzyme 1.0 µg/ml, Leupeptin™ enzyme 1.0 µg/ml, Pefablock™ enzyme 1 mM, 0.1% azide). Oocyst wall antigens were obtained from the back flushing of the 3 µm MicroPrep PCTE™ syringe filter used in the separation of sporozoites after excystation. Separately, both antigens were spotted on PVDF™ (Immunlon-P™ 0.45 µm pore size membrane; Millipore Corporation, Bedford, Mass.) and both reacted with hybridoma supernatant. Bound antibody was detected with anti-mouse peroxidase labeled antibody and visualized with DAB (peroxide/3'3-diaminobenzidine hydrochloride) substrate as taught by Tsang et al., *J. Immunol. Methods* 70:91-100 (1984). In addition to the PVDF™ bound antigen testing of primary hybridomas, hybridomas were screened using indirect fluorescence assays (IFA) to assure the subsequent ability of the monoclonal antibody to recognize sporozoite specific antigens.

For confirmation of sporozoite specificity, reactivity of monoclonal antibodies to intact sporozoites was examined by IFA. Excysted oocysts were spread within 1.0 cm diameter wells, eight per slide, after desiccation (24 hours, 20° C.). Smears were incubated for 25 minutes with 30 µl volumes of hybridoma supernatant (diluted 1:10 in PBS), washed, and incubated with a secondary antibody solution as taught by Arrowood, et al., *J. Parasitol.* 77(2):315-7 (1991). Between incubations, each well was rinsed twice with 50 µl of PBS, which was removed by vacuum aspiration at the edge of each well. The stained well was covered with 15 µl of fluorescence preservative-mounting fluid and a 22×22 mm coverslip, sealed to the slide with mounting cement. Each well was examined using a Zeiss LSM-210 microscope with a 63×/1.4 plan-neofluar objective. Fluorescing objects of the appropriate size and shape were further examined by differential interference contrast microscopy.

Supernatant from positive hybridomas were then screened for ability to preferentially capture sporozoite antigens. The Falcon Assay System Test (FAST™) (Beckon/Dickinson, Falcon Division, Oxnard, Calif.) immuno-assay plate and stick system was used for secondary screening of proliferating hybridomas. Briefly, polystyrene sticks were sensitized with Goat anti-mouse IgG and IgM combined (Boehringer-Mannheim Corporation, Indianapolis, Ind.) each at 1.0 µg-1 ml 100 µl/well in 0.05 M Tris-HCl, 0.3 M KCl, 0.002 M EDTA, pH 8.0±0.1 for 90 minutes. Unbound antibodies were removed by washing using PBS with 0.3% Tween-20 (polyoxyethylenesorbitan monolaurate) (PBS-tw). Fresh anti-mouse IgG/IgM sticks were incubated with a 1:10 hybridoma culture supernatant; PBS-tw for 15 minutes, and unbound antibodies were removed by washing with PBS-tw. Separately, sporozoite antigens and oocyst-wall antigens were then added at 0.01 mg/ml/100 µl in each well, for 30 minutes at room temperature. Unbound antigen was removed by washing with PBS-tw. Polyclonal rabbit anti-*C. parvum* was added at 1:500 dilution, 100 µl/well, in PBS-tw for 15 minutes. Unbound antibodies were removed by washing with PBS-tw. Lastly, a peroxide labeled goat anti-rabbit IgG (Bio-Rad, Hercules, Calif.) was added at a 1:500 dilution 100 µl/well for five minutes. A commercial POD substrate solution (Kirkegaard & Perry Labs, Gaithersburg, Md.) of $H_2O_2$ mixed with buffer and 3,3',5,5'-tetramethylbenzidine (TMB) was added to another 96-well plate at 150 µl/well. Subsequent incubation of the sticks in TMB produced a blue color change in proportion to the amount of POD bound. Hybridomas producing antibodies of interest were cloned by limiting dilution, and grown in static culture using 0.2 µm filter top 75 cm$^2$ culture flasks with 35 ml of Supplemented RPMI 1640 media, 10% [v/v] fetal calf serum (FCS, Hyclone Laboratories, Logan, Utah) in a humidified incubator. Of the monoclonal antibodies screened in this way, one was selected for use in sporozoite antigen capture assays (*C. parvum* viability assay). This monoclonal antibody, isotype IgG1, (Boehringer Mannheim Corp., Indianapolis, Ind.) is named CP7.

For the production of polyclonal antibodies to *C. parvum* antigens, two rabbits were immunized with whole oocyst antigens. For each rabbit, $1 \times 10^6$ oocysts in 1.0 ml of PBS were frozen in liquid nitrogen, then thawed in a 37° C. water bath. This freeze/thaw cycle was repeated four times. Oocysts were mixed 1:1 with FCA and homogenized, similar to the immunizing sporozoite/FCA. Each rabbit received 1.0 ml subcutaneously, divided into two locations. Additional boosts of $1 \times 10^6$ oocysts per rabbit in 1.0 ml of PBS were freeze/thawed four times, as before, and mixed 1:1 with FIA and homogenized, similar to the immunizing sporozoite antigen/FIA. The whole oocyst antigen/FIA was given at weeks 2, 5, and 8. At week 12, each rabbit was boosted with $1 \times 10^6$ oocysts (four cycles freeze/thawing) in 1 ml of PBS without adjuvant, and four days later each rabbit was sacrificed and all sera collected. The sera from these rabbits were checked for activity against the sporozoite antigen captured by MAb CP7. Sera from both rabbits were pooled 1:1 to form the rabbit anti-*C. parvum* polyclonal antibody.

EXAMPLE 2

Optimization of *C. Parvum* Immunoassay

An immunoassay using the antibodies prepared in Example 1 was optimized for the detection of *C. parvum* in a water sample as follows:

Sporozoite Antigen for the Optimization of Ass

To have a standard consistent antigen to optimize reagent concentrations and other assay conditions, a large batch of sporozoite antigen was prepared in much the same way as sporozoite antigen for monoclonal antibody production, as described in Example 1, with the following exceptions. After excystation of $1 \times 10^9$ oocysts, sporozoites were separated from oocyst walls using 3 μm PCTE microfuge spin filter (custom experimental design, Lida Manufacturing Corp., Kenosha, Wis.). To wash away antigens which may have been associated with oocyst walls, separated sporozoites were pelleted and washed twice with PBS. Separated sporozoites were resuspended in PBS and freeze/thawed four times, followed by centrifugation at 21,000×g, and the pellet was discarded. The protein concentration of the supernatant was 0.9 μg/μl. For all optimization assays, 0.006 μg of this sporozoite antigen was used. This yielded roughly the same ECL signal as $1 \times 10^5$ whole oocysts after four freeze/thaw cycles. For storage, proteolytic enzyme inhibitors (Pepstatin A™ 1.0 μg/ml, Leupeptin™ 1.0 μg/ml, Pefablock™ 1 mM, 0.1% azide) were added to the sporozoite antigen. The supernatants were aliquoted in small volumes and stored at −70° C. until used.

To determine the amount of monoclonal antibody CP7 supernatant for antigen capture, commercially available rat anti-mouse IgG1 paramagnetic beads (Dynal, New York, N.Y.) were used. The time of first incubation was limited to 30 minutes. The concentration and mixing volume of monoclonal antibody CP7 was optimized for $8.0 \times 10^4$ beads, as dictated by the ECL™ assay reader, (Igen, Inc., Gaithersburg, Md.). To do this in batches of 20 assays, a saturating amount of monoclonal antibody CP7 supernatant was used, the buffer volume of the mixture was varied to include 30 μl of monoclonal antibody CP7, $1.6 \times 10^6$ beads, 1 ml of ECL assay buffer (0.05 M Tris/HCl, 0.5 M NaCl, 0.75% teleost fish gelatin [TFG, Sigma Chemical Co., St. Louis, Mo.], pH 8.0±0.1). After bead/monoclonal antibody capture incubation, the beads were then washed once with 1 ml of assay buffer, resuspended in 1 ml of ECL assay buffer, and distributed to each assay in 50 μl aliquots ($8.0 \times 10^4$). Monoclonal antibody CP7 supernatant used throughout these experiments was from a single production lot of monoclonal antibody CP7. Subsequent lots showed similar performance.

Polyclonal Rabbit Anti-*C. parvum* Sera

Dilutions of the polyclonal rabbit anti-*C. parvum* antigen, prepared as described in Example 1, were assayed. At each dilution, 0.006 μg of sporozoite antigen was compared to buffer only control and titrated for maximal differential between the two ECL count signal/background ratio. The incubation volume was 300 μl, and the incubation time was 30 minutes. The dilution giving the highest ECL signal/background ratio was 1:800.

Goat Anti-Rabbit Polyclonal Ruthenium Labeled Antibody

Dilutions of commercially available goat anti-rabbit polyclonal $Ru^{++}$ labeled antibody (Igen, Inc., Gaithersburg, Md.) were assayed. At each dilution 0.006 μg of sporozoite antigen was compared to buffer only control and titrated for maximal differential between the two ECL signal/background ratio. The incubation volume was 300 μl, with a incubation time of 30 minutes, at room temperature. The dilution giving the highest ECL signal/background ratio was 1:400.

In Vitro Excystation of Oocysts for Viability Assay:

To evaluate this assay, purified oocysts were spiked into a 1 ml assay sample, in siliconized 1.5 ml microfuge tubes. To each sample 100 μl of excystation buffer (1.0 M sodium acetate, 0.75% sodium taurocholate, pH 5.5±0.1) was added. Samples were mixed well by vortexing and placed in an incubator at 37° C. for two hours in the dark. During the incubation, samples were vortexed at roughly 30 minute intervals. After the incubation, samples were vortexed again and suspensions were then sedimented by centrifugation at 10,000×g for five minutes. 900 μl of the supernatant was transferred to the ECL assay tube (glass 12×75 test tube). The paramagnetic bead/monoclonal antibody CP7 was added to each tube. The bead/MAb was incubated shaking for two hours at room temperature.

Flow Cytometry and Microscopy

To correlate the number of existing oocysts with the counts from the CP7 oocyst viability immunoassay, both flow cytometry and microscopy were independently used to determine the percentage of existing oocysts. For both flow cytometry and microscopy, oocysts were added to 1 ml $dH_2O$, 100 μl of excystation buffer, and 100 μl of 7.5% TFG. Samples were then vortexed well and placed in an incubator at 37° C. for two hours in the dark. During the two hour incubation, samples were vortexed at roughly 30 minute intervals.

Analysis of integrated plots of side scatter, and FITC intensity demonstrated a population of events with high FITC fluorescence. The presence of ghost oocysts (oocysts shells with varying amounts of internal contents/sporozoite) were considered to be responsible for the side scatter skew. Oocysts labeled with wall-specific FITC-monoclonal antibody were gated for forward and side scatter. To calculate the percentage of excysted oocysts in excystation assay, the number of excysted oocysts was divided by the total number of oocyst counts.

All samples were examined with a Zeiss LSM-210™ microscope in a conventional dark field. For enumeration studies, a Zeiss 100×/1.3 plan-neofluor objective with 10× eyepieces was used for all other microscopy. To calculate the percentage of excysted oocysts in the excystation assay, the number of excysted oocysts was divided by the total number of oocyst counts.

Detection of Excysted Sporozoites

To demonstrate that the assay could differentiate viable from non-viable oocysts, on two occasions $3 \times 10^4$ purified and washed oocysts were taken from each of various storage time points (119, 83, and 27 days post-shedding and 151, 115, 50, and 8 days post-shedding). Oocysts from each time point were equally divided and subjected to the following conditions: Excystation of oocysts for two hours at 37° C. in the dark; mechanically disrupted oocysts which had been through four freeze/thaw cycles and non-excysted oocysts maintained at 4° C. No ECL signal was generated from those oocysts maintained at 4° C. The ECL signal from those oocysts which were freeze/thawed was nearly the same, regardless of the time spent in storage. The ECL signal from those oocysts which had been excysted decreased over time.

Detection of Sporozoites by IFA

To visualize the sporozoites and any possible structures that the monoclonal antibody CP7 targeted, oocysts were excysted and affixed to a slide. The monoclonal antibody CP7 supernatant was applied to the slide, followed by a FITC anti-mouse polyclonal. The results indicated that the whole sporozoite was visualized, no discrete structure nor organelle was highlighted.

Reagent Concentration Optimization

To optimize reagents in the CP7 viability assay, each reagent was titrated for maximum ECL signal over background. Optimal concentrations of the monoclonal antibody CP7, rabbit anti-*C. parvum* polyclonal antibody, and ruthenium goat anti-rabbit were determined. The assays to determine the optimal concentrations or reagents for the CP7 viability assay were all done with 0.05 M Tris/HCl, 0.5 M NaCl, pH 8.0, [1.0%]$_f$ BSA as both diluent and wash buffer.

A determination of the optimal amount of monoclonal antibody CP7 to be captured onto the rat anti-mouse IgG1 paramagnetic beads was done in twenty assay batches, to limit assay-to-assay variability. Monoclonal antibody CP7 and $1\times10^6$ beads were incubated with a constant amount of antibody while varying the volume of buffer, effectively varying both the concentration of the paramagnetic beads and concentration of the monoclonal antibody CP7 at the same time while maintaining a fixed amount of each. For $1\times10^6$ paramagnetic rat anti-mouse IgG1 beads the strongest ECL signal for 0.006 μg of sporozoite antigen was achieved at 1000 μl ECL buffer, 1:33 dilution of monoclonal antibody CP7.

To determine the optimal concentration of rabbit anti-*C. parvum* sera in the CP7 viability assay, the sera was titrated (dilutions of 1:400, 1:800, 1:1600, 1:3200, and 1:6400) in assays with 0.006 μg sporozoite antigen and without antigen for the maximum ECL signal/background ratio. A dilution of 1:800 was chosen to provide the highest ECL signal/background ratio.

Optimization of the ruthenium labeled goat anti-rabbit reagent was done in a similar fashion, titrating assays with 0.006 μg sporozoite antigen and without antigen. Two fold dilutions from 1:100 though 1:400 were analyzed in assays with 0.006 μg sporozoite antigen and without antigen to determine the maximum ECL signal/background ratio. The 1:400 dilution was chosen because, with greater dilutions, the background was below the ORIGEN™ ANALYZER'S detection limits.

Use of Teleost Fish Gelatin (TFG) as a Non-Specific Blocking Reagent During Excystation When the monoclonal antibody CP7 viability assay was tested by spiking oocysts into local lake water with varying amounts of mud and bottom sediments, it was found that the ECL signal was completely quenched. To overcome the quenching of the ECL signal in lake sediment samples $[1.0\%]_f$ TFG was added to the excystation buffer as a non-specific blocking reagent. The ECL signal from a lake sample diluted to 1000 NTUs with $1\times10^4$ oocysts was quenched nearly 100%. Although using the TFG quenched some of the ECL signal from $dH_2O$ sample, 65% of ECL signal in $dH_2O$, the signal recovery from the 1000 NTU pond sediment sample was significant (50% of ECL signal in $dH_2O$). The concentration of TFG was later titrated for use in the excystation buffer from $[0\text{-}2.0\%]_f$ and it was found that above $[0.5\%]_f$ TFG did not improve the ECL signal recovery. Therefore, a TFG concentration of $[0.75\%]_f$ was chosen for use in the excystation buffer, and $[1.0\%]_f$ BSA was replaced with $[0.75\%]_f$ TFG as a non-specific blocking reagent in all other buffers.

EXAMPLE 3

*C. Parvum* Immunoassay Sensitivity Analysis

The immunoassay described in Example 2 was analyzed for sensitivity as follows:

Lake Water

To provide a "worst case" example of high turbidity samples, lake water mixed with bottom sediment from three urban lakes in Atlanta, Ga. was used. The lakes were the Kelly Cofer Lake (lake A), Lake Erin (lake B), and Cardinal Dr. (lake C). Samples containing approximately one liter of water, with varying amounts of mud and bottom debris, were collected from each lake. Water and sediments were poured through a U.S. standard sieve, size 30, 0.59 mm (Dual Manufacturing Co., Chicago, Ill.) and stored in 0.1% azide at 4° C. NTUs of each sample were measured at 3125, 90, and 107 NTUs respectively (Turbidimeter, Industrial Chemical Measurement, Hillsboro, Oreg.).

Assay Sensitivity

To evaluate the overall sensitivity of the immunoassay described in Example 2, 1398, 231, and 39 oocysts were each titrated into 3 ml of each lake water sample (lakes A, B, and C) and $dH_2O$ (deionized water, at least 17 MΩ/cm). Each 3 ml sample was then divided into three equal parts, providing a final oocyst number of 463, 77, and 13 oocysts/ml of sample. For each lake water sample at each oocyst titration, one part was freeze/thawed through four cycles representing a total amount of antigen available, a second part was excystated in accordance with the preferred CP7 viability assay described herein representing oocyst capable of existing, and the third part was maintained at 4° C., as a negative control. To evaluate the overall sensitivity, the ECL signal from the freeze/thawed sample was divided by the sample which was maintained at 4° C., yielding a ECL signal/background ratio for each sample. The results for the freeze/thawed samples (total oocysts) are shown in FIG. 2, and the results for the excysted oocysts (viable oocysts) are shown in FIG. 3.

Titration of NTUs in the MAb CP7 Viability Assay with 8.4×103 Oocysts/Assay

To evaluate the maximum NTUs in which the monoclonal antibody CP7 viability assay would be functional, one of the lake A water and sediment samples (starting NTU 3125) was titrated from 10,000 NTUs through 100 NTUs and $dH_2O$. Those NTUs samples above the starting water NTUs were concentrated by centrifugation, and those below the starting sediment were diluted with $dH_2O$. The $dH_2O$ and the 100 NTU sample exhibited nearly identical ECL signal/background ratios of 6.5 and 6.4 respectively. With a ten fold increase in NTUs, the 1000 NTU sample had an ECL signal to background ratio of 3.8. At a further five fold increase to 5000 NTUs, the ECL signal/background ratio drops to about 2. At 10,000 NTUs, the ECL signal/background ratio remains near 2.

Therefore, the working range of this assay is up to 10,000 NTUs in an assay sample. The lower the NTU of the assay sample, the better the ECL signal/background ratio. Samples of less than 100 NTUs were equivalent to $dH_2O$ (0 NTUs) assay samples and thus have even greater sensitivity.

To test the overall detection limit of the CP7 viability assay in the "worst case", the lake water with mud bottom sediment of three different urban lakes and $dH_2O$, as described above, was used. The flow cytometry analysis indicated that, in the oocyst batch used for the sensitivity assay, 52% of the oocysts were excystable. Each of the lake water and bottom sediments were used at the original concentration, (lake A: 3125 NTUs, lake B: 107 NTUs, lake C: 90 NTUs). Oocysts were titrated into each at a concentration of 463, 77, and 13 oocysts/ml sample.

All of the lake water samples demonstrated similar results, with regard to overall detection limits. The ECL signal/background ratio for the freeze/thawed oocysts at 463 oocysts per ml ranged from 7.81 in lake A to 11.34 in the $dH_2O$. At 13 oocysts/ml, the ECL signal/background ranged from 1.38 to 2.92. The ECL signal to background ratio for 244 excystable oocysts/ml for lake water samples ranged from 2.03 in lake C to 2.68 in lake A. The ECL signal to background ratio for 41 excystable oocysts/ml ranged from 1.22 in lake C to 1.96 in lake A. At 7 excystable oocysts/ml, only the dH$_2$O had a ECL signal to background ratio greater than one, at 2.05.

EXAMPLE 4

*C. Parvum* Immunoassay Specificity Analysis

Specificity of monoclonal antibody CP7 The specificity of the monoclonal antibody CP7 was determined by testing its ability to capture antigens from other closely related *Cryptosporidium* species and other protozoan parasites that may be encountered in environmental water samples. Aliquots containing 1×10$^5$ organisms of *C. parvum, C. baileyi, C. muris, C. serpenti, Giardia duodenalis, Eimeria papillate,* and *E. nieschulzi* were exposed to freeze/thaw cycles and assayed. The ECL signal from the freeze/thawed *C. parvum* oocysts was in excess fifty fold that of background. *Cryptosporidium parvum* was the only organism that produced a ECL signal above background as shown in FIG. 4.

EXAMPLE 5

*C. Parvum* Viability in Turbid Environmental Water Samples

*C. parvum* oocysts used for polyclonal and monoclonal antibody production were prepared and optimized according to the methods described in the Examples set forth above.

Environmental Samples

To provide environmental water for evaluating the detection limits of the CP7 viability assay, Pall Gelman Envirochek™ filters (Pall Gelman, Ann Arbor, Mich.) were used to concentrate water samples from two sites. The first site was Kelly Cofer Lake, a 5.5 surface acre urban lake with an initial turbidity of 6.0 NTUs (Turbidimeter, Industrial Chemical Measurement, Hillsboro, Oreg.). The second site was near a municipal water intake for DeKalb Co., Ga., on the Chattahoochee River with an initial turbidity of 3.6 NTUs. At both sites, water was passed through each of five filters until they had clogged 115.8 L and 137.0 L, respectively. Filters were placed on a wrist-action shaker for 30 minutes. The retentate from five filters from each site were pooled and poured through a U.S. Standard Mesh sieve of mesh size 30, 0.59 mm (Dual MFG. Co., Chicago, Ill.). Samples were stored in 0.1% sodium azide at 4° C. NTUs of the pooled samples were 192, and 96, respectively. For assays requiring higher NTUs, the samples were concentrated by centrifugation 20,000×g for 10 minutes. For assays requiring lower NTUs, the samples were diluted with $dH_2O$.

Environmental Sample Assay

To each 2 ml of environmental sample, 200 μl of 10× excystation buffer (0.5 M sodium phosphate, 2.14 M NaCl, 3% porcine gelatin, pH 5.5) and 100 μl of 10% sodium taurocholate (NaT, Sigma Chemical Company, St. Louis, Mo.) were added. One 1 ml of the sample was placed at 37° C. for two hours and mixed thoroughly at 30 minute intervals for excystation. The other 1 ml was maintained at 4° C. After incubation, the samples were sedimented by centrifugation at 10,000×g for 5 minutes. One ml of each supernatant was transferred to an ECL assay tube containing para-magnetic beads/MAb CP7. After a 30 minute incubation, beads were washed with an equal volume of PBS-G. A 1:1000 dilution of rabbit anti-*C. parvum* in PBS-G, 300 μl tube, was added and incubated at room temperature. After 30 minutes, beads were washed, as above, to remove unbound antibody. Finally, a 1:400 dilution of $Ru^{++}$-labeled anti-rabbit antibody, 300 μl/tube, was added and incubated at room temperature. After 30 minutes, each sample was read in the ORIGEN™ ANALYZER (Igen, Inc., Gaithersburg, Md.).

CP7 Viability Assay Evaluation in Environmental Water

To evaluate the CP7 viability assay in the two environmental water sources, the following experiments were conducted. To look at the effects of high NTU water, environmental water samples were concentrated from Kelly Cofer Lake and the Chattahoochee River to 100, 400, and 1000 NTUs, and spiked each with oocysts. When 1000 oocysts were added to the Chattahoochee River samples, the net ECL signal increased slightly from 100 to 1000 NTUs but was not significantly different from the 0 NTUs of $dH_20$ (p value=0.445). However, the effects of increasing NTUs from the environmental sample collected from an urban lake were dramatic. At 100 NTUs of the Kelly Cofer Lake sample, the net ECL signal was reduced by nearly 40%. At 1000 NTUs the net ECL signal was reduced by more than 70%.

Using water from Kelly Cofer Lake and the Chattahoochee River at 200 NTUs, a second experiment was done to determine the ability of the CP7 viability assay (described herein) to detect decreasing numbers of oocysts. The environmental samples from Kelly Cofer Lake, the Chattahoochee River, and $dH_20$ were spiked with 50, 100, 500, 1000, and 5000 fresh (33 days post-shedding) oocysts and assayed in the CP7 viability assay. The results are shown in FIG. 5. In the environmental samples and in $dH_20$, 50 oocysts per ml were detectable. Increasing numbers of viable oocysts gave increasing net ECL counts. In the Chattahoochee River sample, the net ECL counts were comparable to the net ECL counts obtained from oocysts excysted in $dH_20$. However, in the Kelly Cofer Lake sample, the net ECL counts were significantly diminished at all concentrations of oocysts.

To evaluate the effect of the Kelly Cofer Lake sample at 200 NTUs on the detection of sporozoite antigen 50, 100, 500, 1000, and 5000, oocysts were freeze/thawed and the released sporozoite antigen quantitated in the CP7 viability assay. (See FIG. 6). There was no significant difference in the net ECL count between Kelly Cofer Lake and $dH_20$ when looking at 50-1000 oocysts. At 5000 oocysts, the net ECL count from Kelly Cofer Lake was slightly reduced. The loss of ECL-counts in the Kelly Cofer Lake sample was not due to a loss of detectable antigen. Rather, it appears to have been due to an inhibition of excystation in the environmental sample.

The disclosures of all publications cited in this application are hereby incorporated by reference in their entireties in order to more fully describe the state of the art to which this invention pertains.

Modifications and variations of the present method will be obvious to those skilled in the art from the foregoing detailed description. Such modifications and variations are intended to come within the scope of the appended claims.

We claim:

1. A composition comprising monoclonal antibody CP7, produced by the hybridoma deposited with the ATCC as Accession No. CRL-12604, wherein the monoclonal antibody binds an antigen specific to *C. parvum* sporozoites.

2. A kit comprising the monoclonal antibody of claim 1.

3. A method for detecting viable *C. parvum* in a sample, comprising treating the sample to excyst *C. parvum* oocysts and release *C. parvum* sporozoites;

incubating the antibody of claim 1 with the sample; and detecting antibody bound to an antigen specific to a *C. parvum* sporozoite in the sample, wherein the presence of antibody bound to the antigen detects the presence of viable *C. parvum* in the sample.

4. The method of claim 3, wherein the sample is a water sample.

5. The method of claim 3, wherein the sample is a biological sample.

6. The method of claim 3, wherein the method detects *C. parvum* at a concentration of less than 200 oocysts per milliliter.

7. The method of claim 3 wherein the method detects *C. parvum* at a concentration of less than 100 oocysts per milliliter of the sample.

8. The method of claim 4 wherein the sample is a turbid water sample.

9. The method of claim 8, wherein the sample has a turbidity of up to 3,000 nephleometric turbidity units (NTUs).

10. The method of claim 3, wherein treating the sample to excyst *C. parvum* oocysts comprises treating the sample with an excystation buffer, thereby releasing sporozoites from viable oocysts in the sample.

11. The method of claim 3, wherein treating the sample to excyst *C. parvum* oocysts comprises mechanically disrupting oocysts in the sample, thereby releasing sporozoites from viable oocysts in the sample.

12. The method of claim 3, wherein treating the sample to excyst *C. parvum* oocysts comprises incubating the sample at approximately 30° C. to 40° C. in the dark.

13. The method of claim 4, wherein the water sample is a sample of recreational water, natural bodies of water, treated water, or community water reservoirs.

14. The method of claim 3, wherein the monoclonal antibody is directly labeled with a detectable label.

15. The method of claim 14, wherein the detectable label is an enzyme, a radioisotope, a fluorescent label, a luminescent label or a chromogenic substance.

16. The monoclonal antibody of claim 1, wherein the monoclonal antibody is directly labeled with a detectable label.

17. The monoclonal antibody of claim 16, wherein the detectable label is an enzyme, a radioisotope, a fluorescent label, a luminescent label or a chromogenic substance.

* * * * *